United States Patent
Wewers et al.

[11] Patent Number: 5,879,631
[45] Date of Patent: Mar. 9, 1999

[54] GAS DETECTION SYSTEM AND METHOD

[75] Inventors: Frank J. Wewers, Lenexa, Kans.; Kevin EuDaly, Kansas City; Brian K. EuDaly, Lee's Summit, both of Mo.

[73] Assignee: Manning System, Inc., Lenexa, Kans.

[21] Appl. No.: 640,153

[22] Filed: Apr. 30, 1996

[51] Int. Cl.⁶ .................................................. G01N 7/00
[52] U.S. Cl. ............................. 422/98; 422/83; 73/23.2
[58] Field of Search .................. 422/83, 98; 73/23.2, 73/23.31, 31.01, 31.06

[56] References Cited

U.S. PATENT DOCUMENTS

| | | |
|---|---|---|
| 3,864,628 | 2/1975 | Klass et al. . |
| 3,999,122 | 12/1976 | Winstel et al. . |
| 4,040,990 | 8/1977 | Neely ........................................ 260/2.1 |
| 4,171,341 | 10/1979 | Morgan . |
| 4,256,985 | 3/1981 | Goodson et al. . |
| 4,350,660 | 9/1982 | Robinson et al. . |
| 4,407,778 | 10/1983 | Shiratori et al. . |
| 4,481,499 | 11/1984 | Arima et al. . |
| 4,644,333 | 2/1987 | Barendsz et al. . |
| 4,745,796 | 5/1988 | Abdelrahman et al. . |
| 4,839,331 | 6/1989 | Maroldo et al. ........................ 502/416 |
| 4,911,892 | 3/1990 | Grace et al. . |
| 5,057,436 | 10/1991 | Ball . |
| 5,143,696 | 9/1992 | Haas et al. . |
| 5,252,292 | 10/1993 | Hirata et al. . |
| 5,296,196 | 3/1994 | Takeshima . |
| 5,372,785 | 12/1994 | Johnson et al. . |

OTHER PUBLICATIONS

Supelco, Inc., Material Safety Data Sheets for Carboxen 564, pp. 1–3 and Carboxen 569, pp. 1–3, May 6, 1998, Bellefonte, Pennsylvania.

Supelco Data Sheet entitled "Characteristics of Carboxen™ Carbon Molecular Sieves".

*Primary Examiner*—Jeffrey Stucker
*Attorney, Agent, or Firm*—Litman, McMahon & Brown, L.L.C.

[57] ABSTRACT

A gas detection system and method selectively detects a gas in the presence of nonselected contaminant gases. The system includes a housing having a collection chamber and a sampling chamber containing a variable resister and a molecular sieve. A molecular sieve is positioned between the chambers for selectively passing a target gas from the collection chamber to the sampling chamber. An organic molecular sieve permits only selected low molecular weight gases, such as ammonia and carbon monoxide to come into contact with the sensor.

23 Claims, 3 Drawing Sheets

GAS DETECTION SYSTEM AND METHOD

BACKGROUND OF THE INVENTION

1. Field of the Invention

The present invention is broadly concerned with an improved system for selectively detecting low molecular weight gases such as ammonia and carbon monoxide in the presence of a variety of contaminant gases. More particularly, it is concerned with a gas detection system having an organic molecular sieve filter, a semiconductor sensor, an electronic control system, and an alarm. The system of the invention may be used to good effect to continuously monitor for selected low molecular weight gases in hot environments subject to periodic contamination by alcohols, methane, acetic acid, and other nonselected gases.

2. Description of the Related Art

Related art gas detection systems for small molecular weight gases such as ammonia and carbon monoxide lack specificity in that they also recognize a variety of contaminant gases. Such gas detection systems often employ solid state semiconductor gas sensors, broad spectrum devices which are extremely durable and particularly well suited for use in hot environments such as machine rooms. Despite this lack of specificity, in many applications systems employing semiconductor sensors are preferred over those which employ electrochemical sensors, which are more expensive, short lived and may be depleted by a single large gas leak. Such solid state systems are also often preferred over systems employing infrared or ultraviolet light sensors, which are expensive and require complex apparatus to monitor a large area.

For example, ammonia sensors are employed in the food industry, where processing and distributing environments typically include commercial refrigeration systems which employ compressed ammonia gas. Gas detection systems which are currently available to detect leakage of such ammonia refrigerant include sensors which may be tripped by nonammonia-containing gases. Such contaminant gases may emanate from a variety of sources including cleaning chemicals, such as chlorine, ozone, alcohols, and solvents. Alcohol in particular is present in many commercial environments, and heretofore gas detection systems have often been unable to distinguish ammonia gas from alcohols. Other sources of contaminant gases include product off-gassing such as ethylene, and methane gases emanating from food wrappings; use of internal combustion engines, which produce carbon monoxide and unburned hydrocarbons; and air borne, non-gaseous particulate matter such as flour, dust and grease.

In addition, variations in temperature, moisture levels, and air composition, such as low oxygen levels occurring in certain fruit storage areas, may affect the functioning of available gas sensing devices.

Carbon monoxide sensors are employed in both domestic and commercial environments where combustion used to generate heat and air conditioning may also generate toxic gases. Current carbon monoxide gas detection systems may include broad spectrum sensors which may be tripped by other large or small molecular weight gases, a characteristic which increases with the age of the sensor. Maintenance of such systems is expensive and time-consuming, because aging sensors must be replaced at intervals of about every two years in order to compensate for their increased sensitivity. Failure to conduct such frequent maintenance results in false alarms, which may encourage the user to incapacitate the device entirely. In addition, false alarms create the possibility that a true alarm will be ignored.

Previous attempts to employ various kinds of filters in such heated solid state gas sensor devices have been unsuccessful because such filters have been fouled by water vapor present in the ambient atmosphere and negatively affected by the high temperatures caused by the heater component of the device.

Accordingly, there is a need for an improved gas detection system which permits only selected low molecular weight gases to reach a solid state semiconductor sensor, and prevents nonselected, contaminant gases from reaching the sensor.

U.S. Pat. No. 5,296,196 discloses a device for detecting large molecular weight hydrocarbons. The device includes a semiconductor sensor having a zeolite inorganic molecular sieve filter. The pores of the zeolite are doped with a catalyst metal. Small molecular weight hydrocarbons are caught in the pores and oxidized by the metal into water and carbon dioxide, so that only large molecular weight hydrocarbons pass through the filter to the sensor.

U.S. Pat. No. 5,143,696 discloses a device for detecting small molecular weight gases. The device includes an electrochemical sensor having a capacitor coated with a layer of a zeolite inorganic molecular sieve serving as a dielectric. The zeolite is doped with metals for oxidizing or adsorbing of molecules which diffuse into the zeolite pores.

SUMMARY OF THE INVENTION

The present invention overcomes the problems noted above, and provides a greatly improved gas detection system and method which selectively detects a gas in the presence of nonselected contaminant gases.

Broadly speaking, the gas detection system includes a gas sensor and an organic molecular sieve filter which permits only selected low molecular weight gases, such as ammonia and carbon monoxide, to come into contact with the sensor. Preferably, the system includes a solid state semiconductor gas sensor and a housing containing a quantity of one or more organic molecular sieves such as sold under the trademarks CARBOXEN™ 564 or CARBOXEN™ 569. CARBOXEN™ 564 and CARBOXEN™ 569 are trademarks of Supelco, Inc. for its carbonaceous adsorbent molecular sieve materials. These materials are spherical black carbon granules characterized by a 20/45 mesh particle size distribution, specific gravity of 0.600, melting point of 3650° C. and a hydrophobic surface. The CARBOXEN™ 564 sieve (CAS No. 144045-85-2) has a surface area of about 400 $m^2$/gram surface area with micropores measuring about 4 to 40 angstroms and the CARBOXEN™ 569 sieve (CAS No. 145053-81-2) has a surface area of about 485 $m^2$/gram with micropores of about 3 to 40 angstroms. Systems for detection of carbon monoxide employ a quantity of activated charcoal as a prefilter.

OBJECTS AND ADVANTAGES OF THE INVENTION

The principal objects and advantages of the present invention include: providing a gas detection system for detecting low molecular weight gases such as ammonia and carbon monoxide in the presence of other contaminant gases such as hydrogen, alcohols, ethylene, methane, propane chlorine, or ozone; providing such a system which permits detection of a target gas but will not be tripped by contaminant gases; providing such a system which includes a heated semiconductor sensor rather than an electrochemical sensor; providing such a system which includes a solid state semiconductor sensor which requires no catalysts or other consumables; providing such a system which includes a semiconductor sensor which employs a catalyst; providing such a system which is not affected by temperature; providing such a system which is long-lived and cost efficient; which is not impaired by the presence of water vapor; providing such a system which remains stable following continuous exposure to low concentrations of target gases; providing such a system which includes a filter consisting of at least one organic molecular sieve material; providing such a system which includes an activated carbon filter; providing such a system which includes a fiberglass material; providing such a system which includes a pump.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

Referring to the drawings in more detail, the reference numeral 2 generally designates a gas detection sensor embodying the present invention. The sensor 2 is designed for use in a gas detector 4 which generally falls within the semiconductor class characterized by adsorption of a gas on the surface of the sensor 2 which changes the electrical resistance thereof. The resistance change alters an electrical signal passed through the sensor 2 to a preamplifier 6 which provides an output signal 3 on multi-conductor electrical output signal lead 8a. The output signal from the preamplifier is measured across a 100 ohm resister R-1 which is connected to the output signal lead 8a and to a ground lead 8b. A power lead 11 provides power to the detector 4. The output signal lead 8a is connected to a readout/alarm unit 10 which is available from Manning Systems, Inc., Lenexa, Kans. 66214, the assignee of the present application.

Figure 1:
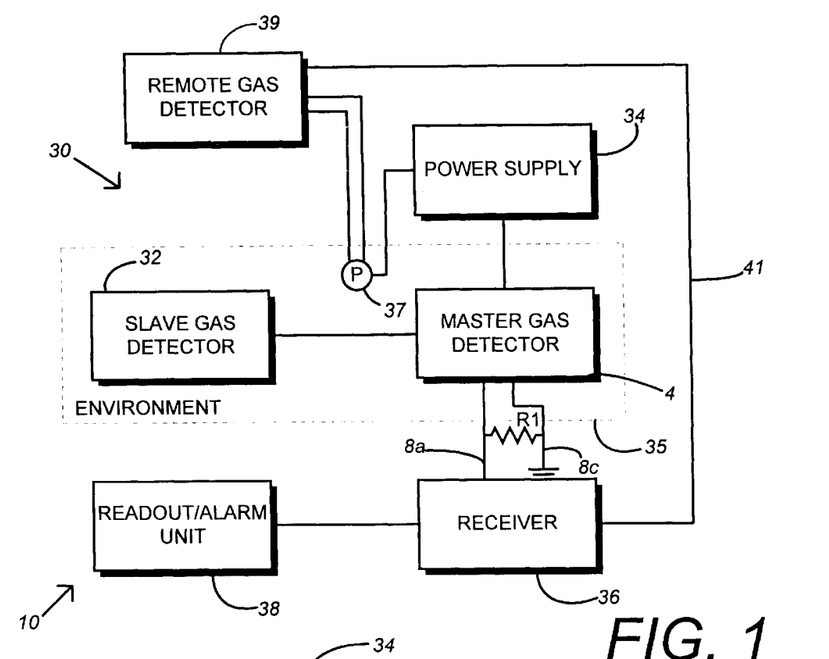
FIG. 1 is a schematic diagram of a gas monitoring system with a pair of gas detection sensors embodying the present invention.
Figure 2:
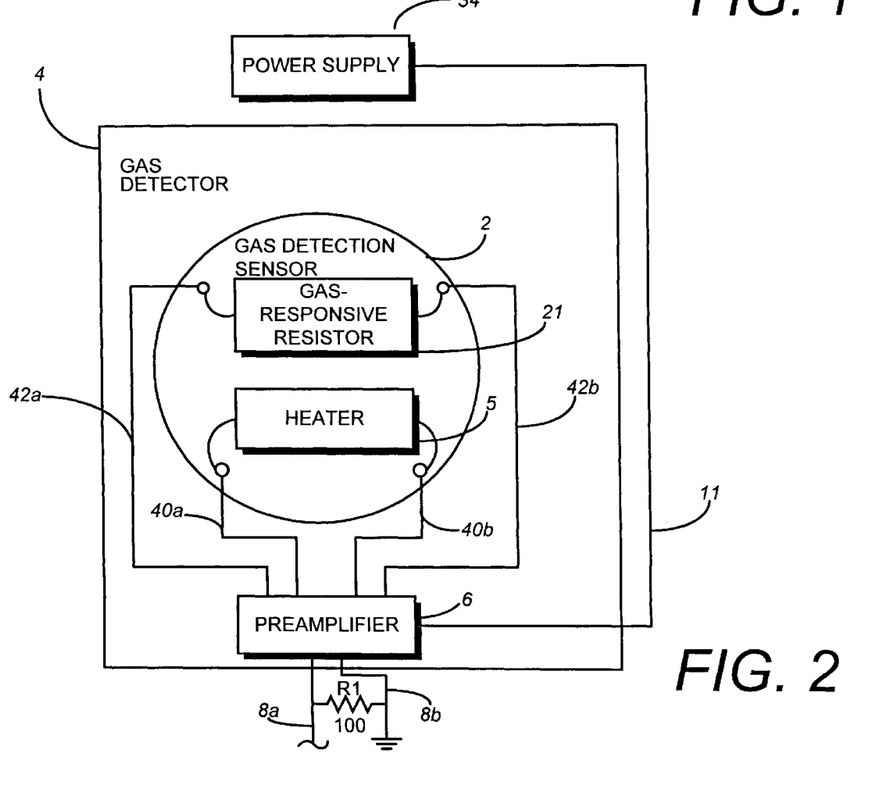
FIG. 2 is a schematic diagram of a gas detector including a single gas detection sensor.

The gas detector 4 can comprise a part of a larger safety/control system for monitoring an ammonia refrigeration plant or other type of installation requiring monitoring and detection of the levels of specific gases, such as ammonia, carbon monoxide, or other low molecular weight gases. A gas monitoring system 30 is shown in FIG. 1 and includes a master gas detector 4 and a slave gas detector 32 connected thereto and located within an environment 35 being monitored. A power supply 34 is connected to the master gas detector 4, which in turn provides an output signal on an output signal lead 8a to a receiver 36. Power supply 34 may also be connected to a pump 37, which is connected to a remote gas detector 39, which provides an output signal 3 on an output signal lead 41 to the receiver 36. The receiver 36 can be connected to a readout/alarm unit 38 which provides a suitable alarm or other output in response to the detection of a predetermined level of target gas.

The gas detector 4 is contained within an enclosure 12. The enclosure 12 can be provided with suitable gaskets (not shown) to substantially seal the interior thereof from the ambient atmosphere of a facility in which the gas detector 4 is installed, or it can be unsealed to allow ambient gas to flow therethrough for reaction with the sensor 2. Such facilities can include equipment for refrigerating, storing, processing and preparing food. In many such facilities the products being stored and processed therein outgas various low molecular weight gases which must be filtered out and excluded by the gas detector 4.

II. Gas Detection Sensor 2

Figures 3, 5:
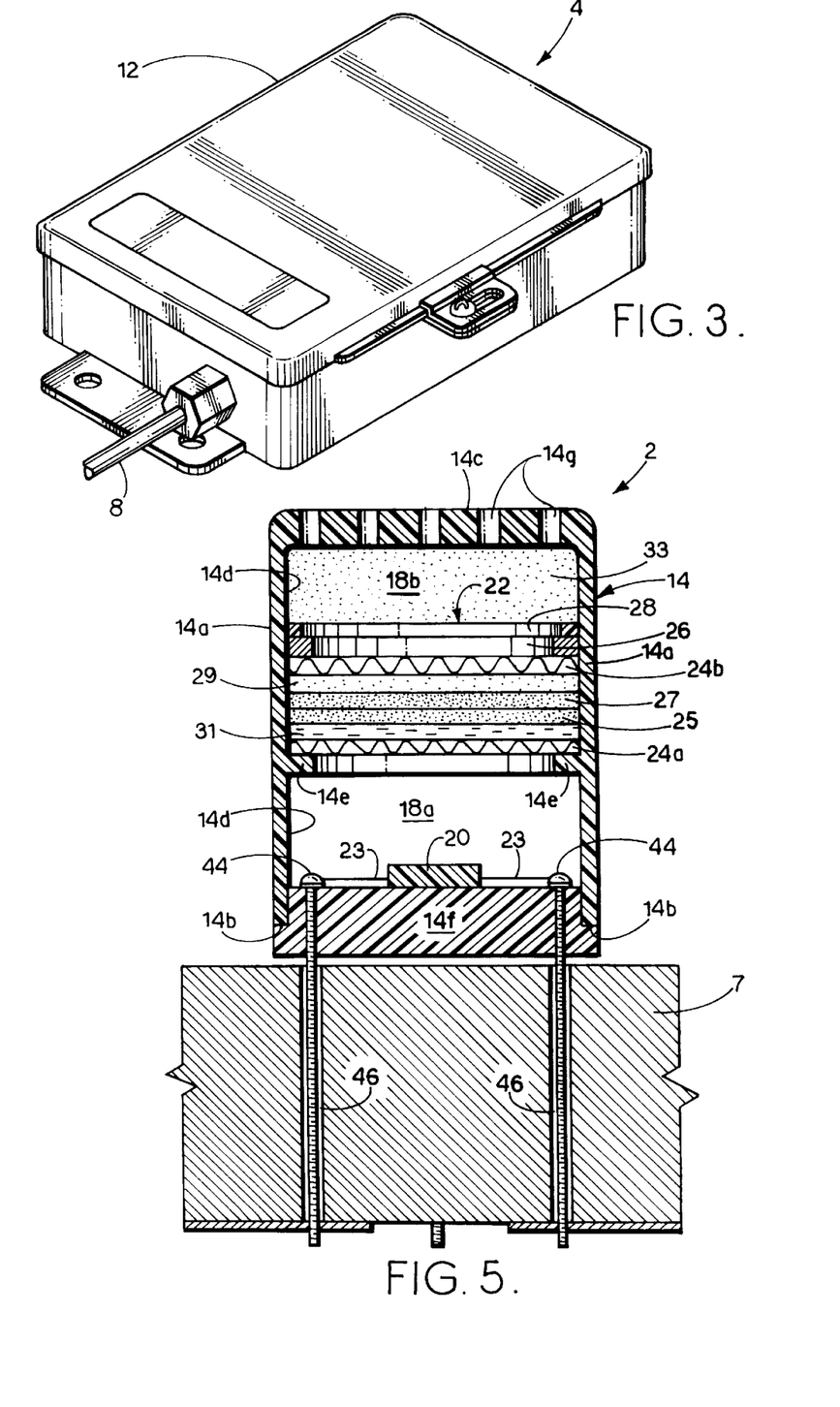
FIG. 3 is a perspective view of the gas detector.
FIG. 5 is a vertical, cross-sectional view of the gas detection sensor, taken generally along line 5—5 in FIG. 4.
Figure 4:
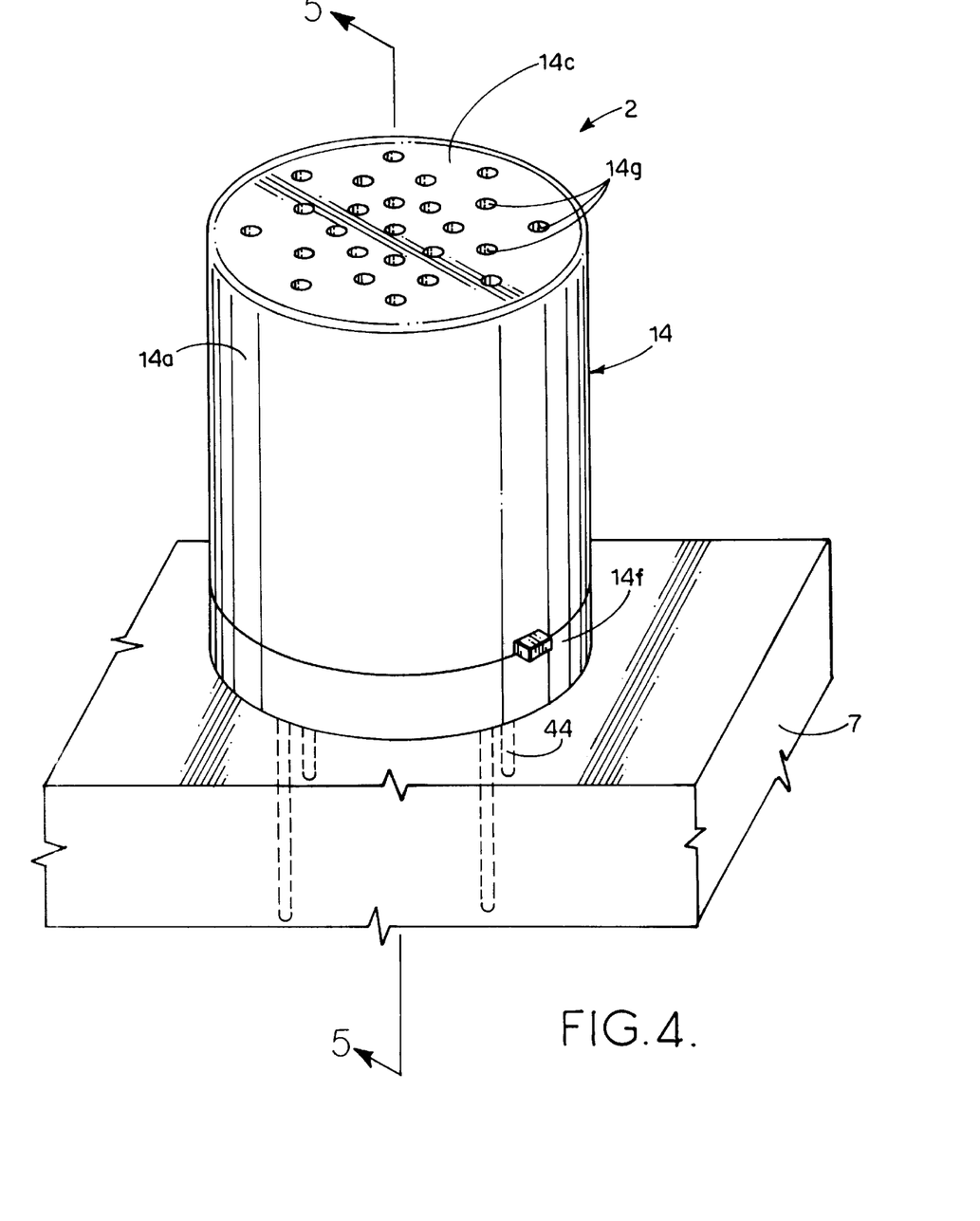
FIG. 4 is a perspective view of the gas detector shown mounted on a circuit board of the gas detector.

The gas detection sensor 2 is mounted in an enclosure 12 as shown in FIG. 3. As shown in FIGS. 4 and 5, the sensor 2 includes a generally cylindrical housing 14 with a sidewall 14a; inner and outer open ends 14b,c; a bore 14d extending between said ends 14b,c; and an annular lip 14e protruding inwardly into the bore 14d and located in spaced relation between the housing ends 14b,c. The housing lip 14e generally divides the bore 14d into an inner, sampling chamber 18a and an outer collection chamber 18b. The housing outer end 14c has a generally flat, circular configuration with a plurality of apertures 14g which provide inlets into the outer collection chamber 18b.

A sensor unit 20 is mounted on a printed circuit card or board 7 and functions electrically as a gas-responsive variable resistor 21. The resistance of the sensor unit 20 is controlled by the presence of a target gas. Such sensor units are well known and various types have been devised for providing variable resistance in response to the presence of predetermined levels of a target gas. Preferred sensors are manufactured by Capteur Sensors and Analyzers Limited and Figaro Engineering, Inc., although any suitable solid state semiconductor sensor may be employed. Such sensors can be created by "doping" a base semiconductor material with a suitable composition, such as a dispersion of a semiconducting metal oxide, for reacting with a target gas. Adsorption of molecules of the target gas on the surface of the metal oxide produces electron transfer. This transfer of electrons results in a change in conductivity of the semiconductor material. For example, the target gas ammonia will cause a sufficient resistance change in a base material comprising a ceramic material doped with tin dioxide.

A sensor housing base 14f is mounted on the sensor housing inner end 14b at a fluid-tight connection with the sidewall 14a whereby the inner sampling chamber 18a is substantially sealed. The sensor unit 20 is mounted on the base 23 within the sampling chamber 18a.

The gas detection sensor mounts a sieve subassembly 22 within the outer, collection chamber 18b. The sieve subassembly 22 includes inner and outer screens 24a,24b enclosing a quantity of a first molecular sieve material 25 and a quantity of a second molecular sieve material 27. Organic molecular sieve materials are preferred because they are not fouled by water vapor and are suitable for use in conditions of high humidity. In addition, they are stable under the elevated temperatures of a heated semiconductor sensor unit. Organic molecular sieve materials such as sold under the trademarks CARBOXEN™ 564 and CARBOXEN™ 569 are especially preferred, although any suitable molecular sieve material may be employed. A quantity of a single molecular sieve may also be employed. Depending on the contaminant gases to be filtered, additional layers of molecular sieve materials may be employed. Those skilled in the art will appreciate that a quantity of a mixture of two or more molecular sieve materials may also be employed. In certain preferred embodiments where the target gas is carbon monoxide, a layer of activated carbon 29 is disposed above the outside molecular sieve layer. In other preferred embodiments a fiberglass plug 31 may be disposed atop inner screen 24a, and additional fiberglass 33 may be packed above outer screen 24b to infill collection chamber 18b and to prevent bowing of outer screen 24b.

Sieve assembly 22 is retained in place by lip 14e and a washer 26 positioned outboard thereof and a snap ring 28 positioned outboard the washer 26 and adapted to grippingly engage the housing sidewall 14a within the housing bore 14d. The positions of the washer 26 and the snap ring 28 are adjustable within the outer, collection chamber 18b whereby various thicknesses of sieve assemblies 22 can be accommodated.

The sensor unit 20 includes the variable resistor component 21 and the heater 5. The heater 5 is connected to the preamplifier 6 by electrical leads 40a,b and is maintained at a relatively constant temperature by a suitable feed-back circuit. The variable resistor 21 is also connected to the preamplifier 6 by a pair of electrical leads 42a,b. The sensor unit electrical leads 40, 42 are connected to respective pins 44 which extend through the housing base 14f and protrude downwardly therefrom for receipt in suitable conductive sockets 46 in the circuit board 7, which in turn are connected to printed circuit leads 48 which electrically couple the sensor unit 20 to the preamplifier circuit 6.

The preamplifier 6 functions to linearize the signal output of the sensor unit 20. The response of the sensor unit 20 is normally exponential, i.e., its conductance is proportional to the square root of the target gas concentration level. Linearizing this signal thus facilitates accurate detection of target gas levels and triggering of responses thereto.

The heater 5 functions to maintain a relatively constant temperature of the sensor unit 20, whose resistance (and conductance) are proportional to temperature.

III. Operation

The gas detection sensor 2 can be retrofit to an existing gas detector 4, or provided as an original component. Moreover, the gas detection sensor 2 can be replaced as necessary, for example, due to the saturation of molecular sieves 25, 27 to the extent that the gas detection sensor 2 loses its effectiveness. In normal operation, heater 5 purges sieves 25, 27 of contaminants so that sensor 2 operates for prolonged periods, and such replacement is infrequent. However, such saturation can occur as a result of prolonged exposure to a target gas or to contaminant gases.

The sensor housing outer end 14c communicates with the ambient atmosphere in the enclosure 12 whereby the outer, collection chamber 18b is filled with ambient gases. The ambient atmosphere from enclosure 12 is transmitted by a pump 37 to a remote gas detector 39.

Installation of the gas detection sensor 2 in a particular facility can be tailored to meet the specific requirements thereof. For example, in coolers and freezers employing ammonia-based refrigeration systems, one or more gas detection sensors 2 (e.g., a master gas detector 4 and a slave sensor 32) can be placed in proximity to components of the refrigeration system which are most susceptible to leakage, such as engines, pumps, valves, etc. Moreover, multiple gas detection sensors 2 can be utilized for purposes of cross-checking and redundancy in a particular environment. In addition, the atmosphere from several distinct environments may be pumped to a single remote gas detector 39 for example, for monitoring the air in several cold rooms.

In the circuit of the gas detector 4, the sensor unit 20 functions as a variable resistor whose resistance either decreases or increases in response to exposure to a target gas. A current passed through the sensor unit 20 by the gas detector 4 circuit thus increases or decreases correspondingly and provides an input to the preamplifier 6. The amplified current provides an output signal from the gas detector 4 to a control system or other components. By way of example, triggering the gas detector 4 can cause an output current therefrom on the output signal lead 8a to increase from approximately 4 milliamps to approximately 20 milliamps upon the detection of a predetermined trigger level of the target gas.

The gas detector 4 can be produced with constant operating conditions for purposes of repeatability, with the adjustments in system sensitivity being accomplished at a receiver 9. Although gases such as ammonia and carbon monoxide are disclosed as targets for the gas detection sensor 2, depending on the specificity of the sensor employed, various other target gases can be detected with the gas detection sensor 2, particularly those having low molecular weight such as hydrogen. The composition of the molecular sieves 25, 27 naturally controls the ambient gases passed to the inner, collection chamber 18a, and the composition of the sensor unit 20 controls the operation of the gas detector 4 including the responsiveness thereof to certain target gases.

The following examples and controls are presented to demonstrate the effect of the invention, although the invention is not limited to these embodiments.

Example I

An organic molecular sieve sold under the trademark CARBOXEN™ 569 was tested to determine its ability to filter out alcohol and other contaminant compounds in an ammonia gas sensor device.

Procedure

Capteur gas sensor devices, model no. 1g-G-S-05-CM-e-06 were employed. Baseline calibration runs 1 and 2 employed an unmodified sensor device. Sample runs 5–8 employed a sensor which was structurally modified generally in accordance with FIG. 5, except that a single layer of sieve material was employed and additional fiberglass material 33 was not employed in between outer screen 24b and housing apertures 14g. Sample runs 3 and 4 employed a sensor which was similarly modified except that no fiberglass material was employed. Sample runs 4–6 and 8 employed a layer of an organic molecular sieve sold under the trademark CARBOXEN™ 569 having a depth of about 2 millimeters (mm); run 7 employed a layer of an organic molecular sieve sold under the trademark CARBOXEN™ 569 having a depth of about 4 mm.

Ambient air and ambient air containing the target gas ammonia or the contaminant gas methanol was delivered to the sensor by a pump at a flow rate of eight liters per minute. Sensor output was calculated from raw sensor response data using the following formulas:

$$K = \frac{C}{(\Delta V)^2} \text{ and } C = K(\Delta V)^2$$

where K is the Sensor Constant, C is the concentration in parts per million (ppm), and V is the voltage in millivolts (mV).

RESULTS

| RUN | SAMPLE GAS | SENSOR RESPONSE (Mv) | SENSOR OUTPUT (ppm NH$_3$) |
|---|---|---|---|
| 1 | 50 ppm ammonia | 0.363 → 0.487 (1 min) | 50 ppm |
| 2 | 10 ppm methanol | 0.365 → 0.416 (1 min) | 8 ppm |
| 3 | 50 ppm ammonia | 0.366 → 0.475 (4 min) | 50 ppm |
| 4 | 10 ppm methanol | 0.369 → 0.360 (4 min) | 0 ppm |
| 5 | 50 ppm ammonia | 0.371 → 0.471 (4 min) | 50 ppm |
| 6 | 10 ppm methanol | 0.369 → 0.361 (4 min) | 0 ppm |
| 7 | 50 ppm ammonia | 0.379 → 0.437 (4 min) | 17 ppm |
| 8 | 50 ppm methanol | 0.373 → 0.406 (4 min) | 5 ppm |

For baseline calibration Runs 1 and 2 using the unmodified sensor device, the sensor responded to both 50 ppm ammonia and 10 ppm methanol at one minute. In Runs 3 and 4, the sensor responded to 50 ppm ammonia, but did not respond to 10 ppm methanol. In runs 5 and 6 the sensor again responded to the ammonia sample, but not to the contaminant methanol gas. In Run 7, the 4 mm layer of an organic molecular sieve sold under the trademark CARBOXEN™ 569 diminished the sensor response to ammonia by 66%. In Run 8, even the high concentration methanol sample caused the sensor to respond only slightly, within 5% standard error.

Conclusion

The organic molecular sieve as sold under the trademark CARBOXEN™ 569 filtered out unwanted contaminant methanol gas while permitting ammonia to pass quickly through to the sensor.

EXAMPLE II

The effect of exposure of an ammonia sensor to saturated alcohol vapor followed by additional prolonged exposure of the housing containing the filter material to saturated alcohol vapor was tested.

Procedure

A pair of Capteur gas sensor devices were modified as described in Example I, runs 5–8. One of the pair was exposed to an atmosphere of saturated methanol vapor for a period of about 21 hours ("exposed sensor"). Seven days later the same housing containing the filter material but not the sensor was exposed to an atmosphere of saturated alcohol vapor comprising 50% methanol and 50% ethanol at about 80° for a period of 49 hours and 42 minutes ("exposed housing"). The exposed sensor and filter material were then combined with each other and with "clean" sensors and filter materials and with unmodified housings containing no filter materials and exposed to ambient air containing either 10 ppm alcohol or 50 ppm ammonia. The sample was delivered to the sensor at a flow rate of 0.8 liters per minute for a period of ten minutes, except runs 5–8, which were for a period of two minutes. Sensor response readings are logarithmic.

RESULTS

| RUN | FILTER | SENSOR | SAMPLE GAS | NET GAIN (Mv) |
|---|---|---|---|---|
| 1 | Exposed | Exposed | methanol | 0.082 |
| 2 | Clean | Clean | methanol | 0.035 |
| 3 | Exposed | Exposed | ammonia | 0.185 |
| 4 | Clean | Clean | ammonia | 0.116 |
| 5 | Empty | Exposed | methanol | 0.073 |
| 6 | Empty | Clean | methanol | 0.041 |
| 7 | Empty | Exposed | ammonia | 0.174 |
| 8 | Empty | Clean | ammonia | 0.117 |
| 9 | Clean | Exposed | methanol | 0.027 |
| 10 | Exposed | Clean | methanol | 0.031 |
| 11 | Clean | Exposed | ammonia | 0.188 |
| 12 | Exposed | Clean | ammonia | 0.125 |

Runs 1–4 consisted of the sensors and housings in their original configuration. The response of the exposed sensor/exposed housing combination to alcohol was 234% of that of the normal sensor. The response of the exposed sensor/exposed housing combination to ammonia was enhanced by 62.3%.

Runs 5–8 consisted of baseline runs of sensors with unmodified housings containing no filter material. The response of the exposed sensor to alcohol was 178% of that of the normal sensor. The response of the exposed sensor to ammonia was enhanced by 148.7%.

Runs 9–12 consisted of reversal of the housings and sensors, e.g., with the exposed housing on the unexposed sensor and the unexposed housing on the exposed sensor. The response of the exposed sensor/clean housing combination to alcohol suddenly dropped at six minutes from a reading of 0.448 Mv to 0.430 Mv, so that at ten minutes the response was 87.1% of that of the clean sensor/exposed housing combination. The response of the exposed sensor/clean housing combination to ammonia was enhanced by 150%.

A graph of the raw sensor readings from Runs 1,2, 9, and 10 shows a comparison of sensor response to alcohol between the exposed and normal filters. The exposed filters in Runs 1 and 10 let more alcohol through to the sensors more quickly than the clean filters in runs 2 and 9. However, the change in response is very slight, about 15–20%. If adjusted for baseline, the curves for unexposed sensor Runs 2 and 10 can be fitted.

A graph of the raw sensor readings from runs 3,4, 11, and 12 show a comparison of sensor response to ammonia between the exposed and normal filters. Curves 3 and 11 plot the nearly identical results of the exposed sensors. If adjusted for baseline, the curves for unexposed sensor Runs 4 and 12 can be fitted.

Conclusion

Sensors used in combination with exposed housings respond to alcohol faster than when used in combination with clean housings. However, the overall change in response is very slight. Whether or not the filter is exposed to alcohol or aged in the presence of a high concentration of alcohol vapor makes little difference in the ammonia response of the sensor.

EXAMPLE III

The organic molecular sieve sold under the trademark CARBOXEN™ 569 was tested in conjunction with activated charcoal to determine its ability to filter out alcohol and other contaminant gases in a carbon monoxide gas sensor device.

Procedure

A pair of Capteur gas sensor devices were modified generally as described in Example I for runs 1,2, and 5,6 and 9A–10, except that for runs 1 and 2 the filter material consisted of a layer of activated carbon 29 in lieu of molecular sieve 27, and for runs 9A, 9B, and 10 the filter material consisted of a layer of about 2 mm of the organic molecular sieve sold under the trademark CARBOXEN™ 569 with a layer of activated carbon 29 packed between outer screen 24b and molecular sieve 27. Sensor number one was employed for runs 1–6, sensor number two was employed for runs 7–10.

The sensors were exposed to ambient air containing either 99.8 ppm carbon monoxide or 10 ppm methanol. The sample was delivered by a pump at a flow rate of 0.8 liters per minute for a period of three minutes for runs 1–5, and 7–8; forty minutes for run 6; three minutes for runs 9A and 9B; and four hours 22 minutes for run 10. Sensor response readings are logarithmic.

RESULTS

| RUN | FILTER | SAMPLE GAS | NET GAIN (Mv) |
| --- | --- | --- | --- |
| 1 | Charcoal | CO | 0.116 |
| 2 | Charcoal | methanol | 0.095 |
| 3 | Empty | CO | 0.105 |
| 4 | Empty | methanol | 0.149 |
| 5 | CARBOXEN ™ 569 | CO | 0.105 |
| 6 | CARBOXEN ™ 569 | methanol | 0.050 |
| 7 | Empty | CO | 0.130 |
| 8 | Empty | methanol | 0.142 |
| 9A | combination | CO | 0.120 |
| 9B | combination | CO | 0.121 |
| 10 | combination | methanol | 0.096 |

Runs 1 and 2 establish the magnitude of the response of the activated carbon filtered sensor to exposure to the sample gas. Runs 3 and 4 were baseline runs of sensor number 1 without filters. Runs 5 and 6 show the effectiveness of the CARBOXEN™ 569 filter in conjunction with activated carbon against carbon monoxide and methanol, respectively. Runs 7 and 8 were baseline runs of sensor number two without filters. Runs 9A, 9B, and 10 compare the effectiveness of the combination filter against methanol and carbon monoxide. Run 9B was a retest of run 9A. Run 10 was a prolonged test. Response continued to increase slightly throughout the test.

A graph of the sensor readings for Runs 1, 3, 5 (sensor number 1) and 7 and 9B (sensor number 2) shows a comparison of sensor response to carbon monoxide with activated charcoal, the organic molecular sieve sold under the trademark CARBOXEN™ 569 and combination filters and with no filter. Curves 1, 3, and 5 are essentially identical. Similarly, curves 7 and 9B are essentially identical when corrected for baseline shift.

A graph of the sensor readings for runs 2, 4, 6, 8, and 10 shows a comparison of sensor response to methanol under the same four filter conditions. Curves 4 and 8 show nearly identical early spikes. Curves 2 and 6 also show similar responses. If corrected for baseline shift, Curve 10 would be similar as well.

Conclusion

Neither activated carbon nor a combination of carboxen 569 and activated carbon demonstrated affected sensor response to gas containing carbon monoxide. Run 6 shows an increased effectiveness of the combination filter against methanol as compared with the activated carbon filter of run 2. Activated charcoal depresses sensor response to methanol. However, the organic molecular sieve sold under the trademark CARBOXEN™ 569 is even more effective as an alcohol filter. The combination the organic molecular sieve sold under the trademark CARBOXEN™ 569/activated carbon filter is even more effective as an alcohol filter.

EXAMPLE IV

Comparative tests of the organic molecular sieve sold under the trademarks CARBOXEN™ 564 and CARBOXEN™ 569 filters in a gas sensor device.

Procedure

A Capteur gas sensor device was modified as described in Example 1, runs 5–8, except that a 1 mm layer of the filter material to be tested was employed. Runs 1 and 4 used an organic molecular sieve sold Carboxen™ 569 filter material; runs 2 and 3 used an organic molecular sieve sold Carboxen™ 564. The sensor devices were exposed to ambient air containing either 50 ppm ammonia or 10 ppm methanol. The sample was delivered by a pump at a flow rate of 0.8 liters per minute throughout the test period. Sensor response readings are logarithmic.

RESULTS

| RUN | FILTER | SAMPLE GAS | TIME | NET GAIN (Mv) |
| --- | --- | --- | --- | --- |
| 1 | CARBOXEN ™ 569 | ammonia | 1 min | 0.041 |
| 2 | CARBOXEN ™ 564 | ammonia | 1 min | 0.043 |
| 3 | CARBOXEN ™ 564 | methanol | 46 min | 0.022 |
| 4 | CARBOXEN ™ 569 | methanol | 20 min | 0.032 |

Runs 1 and 2 show the effectiveness of organic molecular sieves sold CARBOXEN™ 569 and 564 at permitting ammonia gas to reach the sensor. Runs 2 and 3 show the effectiveness of organic molecular sieves sold CARBOXEN™ 569 and 564 at permitting methanol gas to reach the sensor.

Ammonia gas reached the required response by one minute in sensors with, both filters. Both the organic molecular sieves sold under the trademarks CARBOXEN™ 564 and 569 prevented methanol from reaching the sensor.

Conclusion

The organic molecular sieve sold under the trademark CARBOXEN™ 564 demonstrated the same ability to permit ammonia to reach the sensor, while was more effective than CARBOXEN™ 569 at filtering methanol by an about a factor of one.

It is to be understood that while certain forms of the present invention have been illustrated and described herein, it is not to be limited to the specific forms or arrangement of parts described and shown.

What is claimed and desired to be secured by Letters Patent is as follows:

1. A sensor for detecting a target gas, which comprises:
   (a) a housing including a collection chamber with an inlet and a sampling chamber;
   (b) variable resistance means located in the sampling chamber; and
   (c) an organic molecular sieve positioned between said collection and sampling chambers, said organic molecular sieve passing a low molecular weight target gas from the collection chamber to the sampling chamber while filtering out contaminant gases.

2. The sensor according to claim 1, which includes:
   (a) said housing having a generally cylindrical configuration with an outer end including said inlet, an inner end and a housing bore forming said chambers; and
   (b) said collection chamber being located adjacent said outer end and said sampling chamber being located adjacent said inner end.

3. The sensor according to claim 2 which includes:
   (a) said organic molecular sieve being disposed in a generally disk-shaped configuration.

4. The sensor according to claim 2, which includes:
   (a) said housing having a generally annular lip between said collection and sampling chambers; and
   (b) organic molecular sieve retaining means for retaining said organic molecular sieve against said annular lip.

5. The sensor according to claim 4, which includes:
   (a) said organic molecular sieve being positioned outboard said annular lip; and
   (b) said retaining means being positioned outboard said organic molecular sieve.

6. The sensor according to claim 5, which includes:
   (a) said organic molecular sieve retaining means comprising a washer positioned outboard said organic molecular sieve and a snap ring positioned outboard said washer, said snap ring grippingly engaging said housing bore within said collection chamber.

7. The sensor according to claim 1, which includes:
   (a) means for mounting said sensor housing inner end on a circuit board.

8. The sensor according to claim 1, which includes:
   (a) said variable resistance means including a sensor unit with an electrical heater and a semi-conductor resistor.

9. The sensor according to claim 8, which includes:
   (a) said housing having a base; and
   (b) said sensor unit being mounted on said base.

10. A gas detector for detecting a target gas, which comprises:
    (a) an enclosure with an interior;
    (b) gas detection sensor including
        (1) a housing having a collection chamber with an inlet and a sampling chamber;
        (2) a sensor unit having variable resistance means located in the sampling chamber; and
        (3) an organic molecular sieve positioned between said chambers, said organic molecular sieve passing a low molecular weight target gas from the collection chamber to the sampling chamber while filtering out contaminant gases;
    (c) electrical current generation means passing an electrical current through said sensor unit;
    (d) a preamplifier connected to an output of said sensor unit; and
    (e) a receiver connected to said preamplifier and including a read out/alarm unit.

11. The gas detector according to claim 10, which includes:
    (a) said gas detection sensor comprising a first gas detection sensor; and
    (b) a second gas detection sensor connected to said receiver.

12. The gas detector according to claim 10, which includes:
    (a) said gas detection sensor unit having heater means connected to said preamplifier for maintaining said gas detection sensor unit within a predetermined temperature range.

13. The gas detector according to claim 10, wherein said organic molecular sieve is selected from the group consisting of organic molecular sieves sold under the trademarks CARBOXEN™ 564 and CARBOXEN™ 569.

14. The gas detector according to claim 10, which includes:
    (a) said sensor means comprising a semiconductor.

15. The gas detector according to claim 10, which includes:
    a) an output signal lead from said pre-amplifier;
    b) a ground lead from said pre-amplifier connected to ground means; and
    c) a fixed-resistance resistor connected to said output signal lead and said ground lead.

16. A sensor for detecting a low molecular weight gas, comprising:
    (a) a housing enclosing a sampling chamber with an inlet;
    (b) a quantity of an organic molecular sieve positioned in the inlet for passing a low molecular weight gas into the sampling chamber while filtering out contaminant gases; and
    (c) an electrical element located in the sampling chamber and having a resistance which changes in response to the amount of low molecular weight gas in the sampling chamber.

17. The sensor according to claim 16, wherein said organic molecular sieve is selected from the group consisting of organic molecular sieves sold under the trademarks CARBOXEN™ 564 and CARBOXEN™ 569.

18. The sensor according to claim 16, wherein said low molecular weight gas is selected from the group consisting of ammonia, carbon monoxide and hydrogen.

19. The sensor according to claim 16, wherein said contaminant gases are selected form the group consisting of alcohols, ethylene, methane, propane, chlorine, and ozone.

20. A low molecular weight gas detector, comprising:
    (a) an enclosure with an interior;
    (b) a gas detection sensor including
        (1) a housing enclosing a sampling chamber with an inlet;
        (2) a quantity of an organic molecular sieve positioned in the inlet for passing a low molecular weight gas into the sampling chamber while filtering out contaminant gases;
(3) an electrical element located in the sampling chamber and having a resistance which changes in response to the amount of low molecular weight gas in the sampling chamber;
(c) an electrical current generator passing an electrical current through said electrical element;
(d) a preamplifier connected to an output of said electrical element; and
(e) a receiver connected to said preamplifier and including a read out/alarm unit.

21. The gas detector according to claim 20, wherein said organic molecular sieve is selected from the group consisting of organic molecular sieves sold under the trademarks CARBOXEN™ 564 and CARBOXEN™ 569.

22. The sensor according to claim 20, wherein said low molecular weight gas is selected from the group consisting of ammonia, carbon monoxide and hydrogen.

23. The sensor according to claim 20, wherein said contaminant gases are selected form the group consisting of alcohols, ethylene, methane, propane, chlorine, and ozone.

* * * * *